United States Patent [19]
Berry et al.

[11] Patent Number: 6,014,451
[45] Date of Patent: Jan. 11, 2000

[54] REMOTE IMAGING SYSTEM FOR PLANT DIAGNOSIS

[75] Inventors: James A. Berry, Waukee; William E. Dolezal, Ankeny; Adda C. Sayers, Des Moines, all of Iowa

[73] Assignee: Pioneer Hi-Bred International, Inc., Des Moines, Iowa

[21] Appl. No.: 08/953,331

[22] Filed: Oct. 17, 1997

[51] Int. Cl.[7] .................................................. G06K 9/00
[52] U.S. Cl. .......................................... 382/110; 382/128
[58] Field of Search ................................... 382/100, 110, 382/128; 348/79, 80, 143

[56] References Cited

U.S. PATENT DOCUMENTS

| | | | |
|---|---|---|---|
| 5,216,596 | 6/1993 | Weinstein | 364/413.02 |
| 5,253,302 | 10/1993 | Massen | 382/1 |
| 5,297,034 | 3/1994 | Weinstein | 364/413.02 |
| 5,528,703 | 6/1996 | Lee | 382/257 |
| 5,836,877 | 11/1998 | Zavislan | 600/407 |
| 5,841,883 | 11/1998 | Kono et al. | 382/110 |

FOREIGN PATENT DOCUMENTS

| | | | |
|---|---|---|---|
| 2726367 | 5/1996 | France | G01N 21/84 |

OTHER PUBLICATIONS

Plaisant et al., "Exploring Remote Images: A Telepathology Workstation," ACM Conf. Proc. on Human Factors in Computing Systems, Apr. 1993, p. 518.

Schmid et al., "Image Processing to Overcome Channel Capacity Limitations in Telemicroscopy," IEEE Proc. 13th Int. Conf. on Pattern Recognition, vol. 3, Aug. 1996, pp. 929–933.

Young, "Digital Cameras are Latest Tool for University Extension Agents," *The Chronicle of Higher Education*, Nov. 20, 1998, pp. A21–A22.

"Plant Doctors Say Take 2 Pictures, Call in the Morning," *The Wall Street Journal*, Dec. 9, 1998, p. F2.

Web site: "Distance Diagnostics Through Digital Imaging," at the Univesity of Georgia, College of Agricultural and Environmental Sciences, homepage URL: http://www.ces.uga.edu/distance—diagnostics/index.html, printed Apr. 19, 1999.

Mcclean et al., *Promenade: Networked Query and Retrieval of Horticultural Images*, Online Information 94. 18th International Online Information Meeting, Jun. 12, 1994, 457–468, XP–002091819, School of Library and Information Science, University of Pittsburgh, USA.

Yialouris et al., An Expert System for Tomato Diseases, *Computers and Electroinics in Agriculture*, Jan. 1996, 61–76, vol. 14, Elsevier, Nethlands.

Fotedar et al., Plant Condition Remote Monitoring Technique, International Geoscience and Remote Sensing Symposium Remote Sensing for a Sustainable Future, May 28, 1996, 239–242, vol. 1, Lincoln, NE.

*Primary Examiner*—Andrew W. Johns
*Attorney, Agent, or Firm*—Alston & Bird LLP

[57] ABSTRACT

Provided herein are systems and methods for diagnosing plant anomalies found at remote locations using video imaging. A diagnostic technician at a diagnostic station is capable of diagnosing a plant anomaly and recommending a course of action based upon images trasmitted from a remote workstation. The diagnostic technician has access to a database of images and/or descriptions of plant pathogens, lesions and other anomalies to assist in making a diagnosis. It is further preferred that field data relevant to the diseased plant sample is collected at the remote workstation and provided to the diagnostic technician for diagnostic purposes.

40 Claims, 1 Drawing Sheet

REMOTE IMAGING SYSTEM FOR PLANT DIAGNOSIS

FIELD OF THE INVENTION

The present invention provides systems and methods for diagnosing plant diseases at a remote site by remote video imaging. In particular, the present invention relates to systems and methods for diagnosing diseases, abnormalities, anomalies, and the like in plants.

BACKGROUND OF THE INVENTION

The incidence of foliar plant pathogens has increased in recent years, and the cost of managing foliar plant diseases has inflated field production costs. In particular, seed corn fields have encountered numerous plant pathologic problems. The increased incidence of plant pathogens has brought about the need for treating seed fields with foliar fungicides such as TILT®.

Research indicates that seed field yield losses from foliar diseases can reach as high as 58% if infection occurs early and environmental conditions favor disease spread and development. Early detection and diagnosis of the disease with timely applications of a foliar fungicide are necessary to avoid such devastating losses. Rapid diagnosis of plant pathogens is also critical because some fungicides cannot be applied after a certain stage in the plant's maturity. In addition, some genetic leaf abnormalities (e.g., lesion mimics, leaf speckling, heat stripe, genetic stripe) look similar to symptoms produced by plant pathogens. A misdiagnosis of a genetic abnormality as a plant pathogen can be very costly—one application of TILT® will typically cost $15.00–$16.00/acre.

With respect to corn, Gray Leaf Spot (*Cercospora zeae-maydis*) is now the leading plant pathogen found in seed corn fields, and the spread of Gray Leaf Spot throughout U.S. seed corn production locations has increased substantially over the past several years. Early detection and identification of Gray Leaf Spot in seed corn fields is essential to reverse this trend and suppress this plant pathogen.

Accurate identification of plant pathogens within a field has typically been done by an agronomist with support from a plant pathology laboratory. In most situations, however, a plant pathologist is not on-site at a seed crop production location. Moreover, most seed crop production locations are at a distance from facilities that specialize in the identification of plant pathogens. This distance between the field site and the diagnostician creates a significant increase in turnaround and response times. Plant or pathogen samples must be sent from the seed crop production location to the plant pathology diagnostic laboratory by transportation or mail. Samples routinely take 1–4 days to arrive at the laboratory. An additional 2–7 days are needed for analysis and 1–3 more days for response. At best, a diagnosis takes four days, and at worst, fourteen days or more. More recently, with overnight delivery and electronic mail, analysis times have fallen to the range of 3–5 days. However, there are significant problems attendant to transporting or shipping diseased plant material over long distances, in particular, across state or national borders.

In addition to the need for faster turn-around times for sample analysis, the need to provide pathology support on a global scale has increased. U.S. Pat. Nos. 5,216,596 and 5,297,034 to Weinstein disclose telepathology diagnostic systems whereby a diagnostician can evaluate animal tissue specimens at a remote site and make a diagnosis therefrom. The present invention meets a need in the art for plant disease diagnosis at remote sites.

SUMMARY OF THE INVENTION

The present invention provides a remote imaging system for diagnosing plant anomalies at locations remote from a plant pathology diagnostic laboratory. According to the present invention, a technician at a plant pathology diagnostic laboratory makes diagnosis of plant anomalies found at the remote location by viewing video images of macro- and microscopic views of plant lesions, pathogens, and abnormalities found therein. In preferred embodiments of the invention, the diagnostic technician has access to a database of plant anomalies and abnormalities to assist in diagnosis. It is further preferred that field data relevant to the plant sample is collected at the remote location and provided to the diagnostic technician for the purpose of diagnosis.

These and other aspects of the present invention are discussed in more detail in the description of the invention below.

DETAILED DESCRIPTION OF THE PREFERRED EMBODIMENTS

Figure 1:
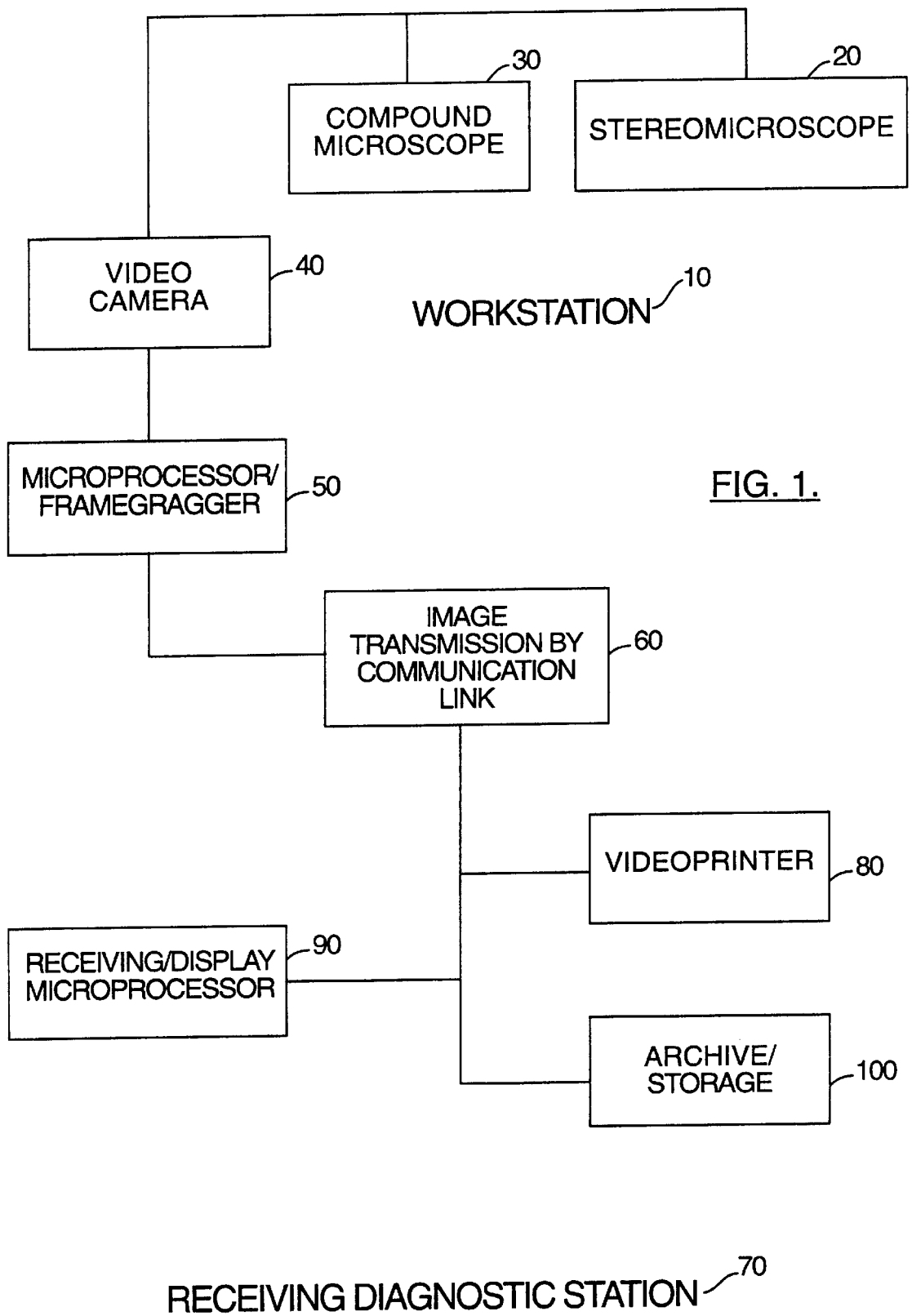
FIG. 1 is a schematic representation of a remote video imaging system for the diagnoses of plant anomalies.

Methods and compositions for diagnosing plant anomalies are provided at locations remote from a plant diagnostic laboratory. A technician at a remote laboratory or site makes a diagnosis of plant anomalies by capturing video images of the plant, plant part, plant lesion, plant pest, plant anomaly and the like and transmitting these images to the plant diagnostic technician.

By plant anomalily is intended plant abnormalities including genetic, environmental, and the like; plant damage including insect injury, chemical injury, environmental injury and the like; plant diseases; plant pathogens; plant pests; etc. An image of the plant, plant part, plant lesion, plant pest, etc. is transmitted to a technician at another location. Thus, diagnostic technicians of the invention include pathologists, agronomists, geneticists, entomologists, and other scientists needed to make a diagnosis and recommended course of action.

A plant pathology diagnostician relies on a combination of gross symptomatology and microscopic images to make a disease diagnosis. The present invention provides systems and methods whereby a diagnostic technician can diagnose diseases and other plant anomalies in plants without physically handling the plant tissue. There are several benefits derived from implementation of a remote site plant pathology (RSPP) laboratory. First, the turn-around time for verification of plant pathogens is reduced as compared with conventional diagnostic techniques. Furthermore, remedial steps can be taken in a more timely manner, which in turn will give increased yields.

The present invention finds use in diagnosing anomalies in any type of plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia*

*sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, vegetables, ornamentals, and conifers.

Vegetables include tomatoes (*Lycopersicon esculentum*), lettuce (e.g., *Lactuea sativa*), green beans (*Phaseolus vulgaris*), lima beans (*Phaseolus limensis*), peas (Lathyrus spp.) and members of the genus Cucumis such as cucumber (*C. sativus*), cantaloupe (*C. cantalupensis*), and musk melon (*C. melo*). Ornamentals include aza.lea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*dianthus caryophyllus*), poinsettia (*Euphorbia pulcherima*), and chrysanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (e.g., corn, alfalfa, sunflower, canola, soybean, cotton, peanut, sorghum, wheat, tobacco etc.), more preferably corn and soybean plants, yet more preferably corn plants. Moreover, the present invention finds use in diagnosing diseases in any plant tissue (i.e., roots, stem, leaves, flowers, seed).

In one embodiment, the present invention is used to diagnose pathogenic diseases in plants. Pathogens of the present invention include, but are not limited to, viruses or viroids, bacteria, fungi, and the like. Viruses include any plant virus such as tobacco or cucumber mosaic virus, ringspot virus, necrosis virus, maize dwarf mosaic virus, etc. Specific plant pathogens for the major crops include: Soybeans: *Phtophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffusa*, *Fusarium semitectum*, *Phialophora gregata*, Soybean mosaic virus, *Glomerella glycines*, Tobacco Ring Spot Virus, Tobacco Streak virus, *Phakospora pachyrhizi*, *Pythium aphanidermatum*, *Pythium ultimum*, *Pythium debaryanum*, Tomato spotted wilt virus, *Heterodera glycines Fusarium solani*; Canola: *Albugo candida*, *Alternaria brassicae*, *Leptosphaeria maculans*, *Rhizoctonia solani*, *Sclerotinia sclerotiorum*, *Mycosphaerella brassiccola*, *Pythium ultimum*, *Peronospora parasitica*, *Fusarium roseum*, *Alternaria alternata*; Alfalfa: *Clavibacter michiganese* subsp. *insidiosum*, *Pythium ultimum*, *Pythium irregulare*, *Pythium splendens*, *Pythium debaryanum*, *Pythium aphanidernatum*, *Phytophthora megasperna*, *Peronospora trifoliorum*, *Phoma medicaginis* var. *medicaginis*, *Cercospora medicaginis*, *Pseudopeziza medicaginis*, *Leptotrochila medicaginis*, *Fusarium oxysporum*, *Rhizoctonia solani*, *Uromyces striatus*, *Colletotrichum trifolii* race 1 and race 2, *Leptosphaerulina briosiana*, *Stemphylium botryosum*, *Stagonospora meliloti*, *Sclerotinia trifoliorum*, Alfalfa Mosaic Virus, *Verticillium albo-atrum*, *Xanthomonas campestris* p.v. *alfalfae*, *Aphanomyces euteiches*, *Stemphylium herbarum*, *Stemphylium alfalfae*; Wheat: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, High Plains Virus, European Wheat Striate Virus; Sunflower: *Plasmophora halstedii*, *Sclerotinia sclerotiorum*, Aster Yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* pv. *carotovora*, *Cephalosporium acremonium*, *Phytophthora cryptogea*, *Albugo tragopogonis*; Corn: *Fusarium moniliforne* var. *subglutinans*, *Erwinia stewartii*, *Fusarium moniliforme*, *Gibberella zeae* (*Fusarium graminearum*), *Stenocarpella maydis* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella zeae*, *Colletotrichum graminicola*, *Cercospora zeae-maydis*, *Cercosporc sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganense* subsp. *nebraskense*, *Trichodenna viride*, Maize Dwarf Mosaic Virus A & B, Wheat Streak Mosaic Virus, Maize Chlorotic Dwarf Virus, *Claviceps gigantea*, *Claviceps sorghi*, *Pseudomonas avenae*, *Erwinia chrysanthemi* pv. *zea*, *Erwinia corotovora*, Corn stunt spiroplasma, *Diplodia macrospora*, *Sclerophthora macrospora*, *Peronosclerospora sorghi*, *Peronosclerospora philippinensis*, *Peronosclerospora maydis*, *Peronosclerospora sacchari*, *Spacelotheca reiliana*, *Physopella zeae*, *Cephalosporium maydis*, *Caphalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum*, *Colletotrichum graminicola* (*Glomerella graminicola*), *Cercospora sorghi*, *Gloeocercospora sorghi*, *Ascochyta sorghina*, *Pseudomonas syringae* p.v. *syringae*, *Xanthomonas campestris* p.v. *holcicola*,

*Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane Mosaic Virus H, Maize Dwarf Mosaic Virus A & B, *Claviceps sorghi, Claviceps africana, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

In one preferred embodiment of the invention, the remote imaging diagnostic systems and methods disclosed herein are used to diagnose diseases caused by pathogenic fungi in corn plants.

In other embodiments, the present invention finds use in diagnosing non-pathogenic diseases, such as genetic striping, lesion mimics, genetic speckling, or heat stripe. Alternately, the present invention may be used to diagnose herbicide injury. As further alternatives, the present invention finds use in weed and insect identification, as well as pollen, seed and tassel imaging. The invention can also be used to diagnose chemical injury, genetic abnormalities, and other plant anomalies.

As noted above, the methods of the invention can be utilized to diagnose insect and disease pests. For purposes of the present invention, pests include but are not limited to insects, pathogens including fungi, bacteria, nematodes, viruses or viroids, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera. Insect pests of the invention for the major crops include but are not limited to: Maize: *Ostrinia nubilalis*, Eurooean corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agroniyza parvicornis*, corn bloth leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, leser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug: *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, plae western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubruin*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton boll worm; *Helicoverpa zea*, cotton bollworm; *Spodoptera exigua*, beet armyworm; *Pectinophora gossypiella*, pink bollworm; *Anthonomus grandis*, bool weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhoper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton boll worm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid.

The basic components of the system include a workstation, a receiving station and a communication means to transmit images between the stations. The workstation comprises means for videomicroscopy including, for example, microscopes, stereomicroscopes, macroscopes, video cameras, videomicroscopes, optical accessories, digital microprocessor with a framegrabber board, PC, and the like. The receiving station comprises a means for viewing the images produced at the workstation such as a display microprocessor. In this manner, the diagnostic technician present at a single receiving station can view and diagnose plant symptoms from one or several remote locations.

The system may additionally comprise a bidirectional communication means to link the microscope with the receiving station. Additionally, the system may include a robotically controlled microscope at the workstation equipped with a video camera means for collecting video signals from the microscope. Where the system employs bidirectional communication, the technologist is able to generate control signals which are sent over the bidirectional communication means to remotely control the microscope by a control means. In this manner, the diagnostic technician at the receiving station can view the specimen remotely and also can control all the microscope functions.

FIG. 1 presents a schematic overview of one remote video imaging system of the present invention. The system involves a remote workstation 10 and a centrally-located diagnostic station 70 (the receiving station). In the embodiment presented in the FIGURE, the workstation 10 is equipped with a stereomicroscope 20, a compound microscope 30, and a video camera 40 for capturing images from the two microscopes, and a microprocessor equipped with a framegrabber board and a display monitor 50. The images are transmitted by a communication link 60 to the diagnostic station 70. The diagnostic station 70 is equipped with a microprocessor 90 for receiving and displaying the transmitted images from the workstation 10, a video printer 80 for printing hard copies of the transmitted images, and an archive 100 for storing the transmitted images and associated data.

As used herein, a "remote workstation" is a facility with basic laboratory equipment and personnel, but without an advanced plant diagnostic laboratory or plant diagnostic technician. Typically, the workstation is located in relatively close proximity to research or production growing sites, production facilities or large growing areas. A "diagnostic station", in contrast, does have sophisticated equipment and trained diagnostic technicians to make accurate diagnoses. Generally, the diagnostic station will provide diagnostic services to more than one remote workstation. For example, there may be one diagnostic station per country, per state or per county that supports numerous workstations throughout the state, county, or even throughout the country. A diagnostic station may also provide diagnostic services to workstations in other states or other countries.

In the methods of the invention samples can be collected at remote sites and viewed at the diagnostic station. Samples of the invention include whole plants, plant parts such as leaves, tassels, roots, etc., plant lesions, insects, seeds, and the like.

According to one aspect of the present invention, putative diseased plants, plant tissues, or other samples for analysis are brought directly into the remote workstation for analysis. Where the samples are from diseased plants the samples are taken from the plant by a trained technician. One or more pieces of tissue bearing representative lesions are removed from the plant. The tissue is placed in petri dishes or other containers and incubated by conventional pathological techniques to promote growth of any pathogenic organisms in the lesion. In the case of pathogenic fungi, the lesion-bearing tissue is placed in a petri dish between pieces of moist filter paper and incubated at room temperature for 24 to 72 hours until sporulation is evident under the stereomicroscope.

After culturing, the tissue pieces are viewed under low magnification (typically 10× to 70×) with a stereomicroscope. The stereomicroscope combined with the video camera and video microprocessor with a framegrabber board are used to capture an overall view of the lesion and the pathogen/host relationship on the sample. The stereomicroscope permits observation of fruiting structures of a fungal pathogen or exudate of bacterial pathogens.

The lesions on the cultured tissue are then scraped and microscope slides are prepared therefrom. The microscope slides are viewed under higher magnification (typically 100× to 400× or 1000×) with a compound microscope. The higher magnification of the compound microscope allows visualization of details of fungal spores and bacteria. With respect to fungal pathogens, these high magnification images are critical to accurate diagnosis as most fungal taxonomy is based on minute characteristics of the spore (e.g., size, color, shape, markings, protuberances, etc.). In the case of pathogenic bacteria, additional diagnostic tests will generally be performed. The plant tissue lesions can be probed and the bacteria amplified in liquid or solid media. The amplified bacteria are then subjected to a panel of standard diagnostic tests, as are known to those skilled in the art, by technicians al the remote workstation. The results of these simple tests will further assist the technician in making a diagnosis.

Both the stereomicroscope and compound microscope are fitted with mounts compatible with a video camera. The video camera combined with a digital microprocessor with a framegrabber board captures or collects images of the sample from both microscopes. Preferably, the video camera will be a single chip RGB type. It is the combination of gross and microscopic observations of the sample that are critical to the diagnostic technician in making an accurate diagnosis.

The video camera can also serve as a macroscope. In a preferred embodiment of the invention, macroscopic images of the sample, such as diseased plant or tissue are collected to give the diagnostic technician information as to overall symptomatology. In identifying diseases, lesion size, shape and color all assist in accurate disease identification. The macroscope is typically a camcorder, video camera, or digital camera. Additionally, a color scanner could also be used.

The inventive systems and methods disclosed herein also find use in the diagnoses of viruses or obiotic anomalies, such as genetic striping, genetic speckling, lesion mimics or heat stripe. Alternately, the present invention may be used to diagnose herbicide, chemical, insect, or environmental injury. The absence of a bacterial or fungal pathogen taken together with the macro- and microscopic views of the lesions and the relevant field data will enable the diagnostic technician to make an accurate diagnosis of these other plant anomalies.

While black and white images can be transmitted, in preferred embodiments of the invention the video camera feeds color images from the microscopes into an in-line microprocessor, for example, a personal computer (PC). The microprocessor is equipped with a framegrabber board to capture the images from the video camera source. Color images can be viewed and manipulated in real time on the computer's display monitor. The framegrabber board is also compatible with a camcorder, scanner or other peripheral imaging devices.

The microprocessor has software capabilities to manipulate and annotate images. For example, the image can be cropped or can be annotated with information, such as the date, hybrid, variety, inbred, field number, etc. IMAGE CENTRAL®, THUMBSPLUS®, PHOTOSHOP®, and L-VIEW PRO® are exemplary software programs providing these capabilities. The annotated image can be imported into a word processing program, such as MICROSOFT WORD® or to a web site. The microprocessor can also transmit images by modem.

The images captured by the video camera are fed into the microprocessor, and are then transmitted to the diagnostic station for diagnosis by a diagnostic technician. The images can be transmitted by any means known in the art, including fiber optic cables, coaxial cables, and satellite. Preferably, the images are transmitted such that they are displayed in real time at the diagnostic station (e.g., by satellite).

A bidirectional communication means by which the remote sites can be linked to the diagnostic center or workstation is optionally provided. In general, bidirectional communication means will include broadband transmission for sending the video signal from the remote worstation to the diagnostic station. The communication means will also require two-way transmission for exchanging data between the two sites. Preferably, the communication means will also provide for two-way audio transmission. See, for example, U.S. Pat. Nos. 5,297,034; 5,216,596; and 5,528,703.

In preferred embodiments of the invention, the video images are "tagged" or attached to an electronic form containing field data. Preferably, a software program such as MICROSOFT WORD® or ACCESS® is used to create the form. Relevant information may include: grower, field number from which the sample came, weather conditions, inbred, hybrid, variety, incidence of disease in the field, prior disease history of the field, the identity of the individual collecting the sample, and the identity of individuals who should receive a diagnostic report from the technician. The images and field data form are preferably transmitted to the diagnostic center together. The field information further assists the diagnostic technician in making a diagnosis. Moreover, after the images and data are archived, they provide a resource to assist technicians in monitoring the incidence and progression of plant diseases and pathogens.

The diagnostic station is equipped with a microprocessor, a video printer, or preferably both, to receive and display color images transmitted from the workstation. The diagnostic technician can view the transmitted images and tagged field data on a display monitor or by printing off a hard copy of the images from the video printer. In preferred embodiments of the invention, the diagnostic technician views the images in real time, and more preferably has robotic controls to manipulate the microscope and stereomicroscope at the remote workstation from the diagnostic station. According to this embodiment of the invention, the diagnostic technician will have control over the movement of the stage as well as the magnification, focus and illumination of the microscopes. In this way, the diagnostic technician has a level of control in viewing the specimen microscopically comparable to that which he would have if he had the specimen in his possession. Methods of robotically controlling a microscope at a remote location are described in U.S. Pat. Nos. 5,216,596 and 5,297,034 to Weinstein.

It is further preferred that the diagnostic station has a database (paper and/or electronic) of plant pathogens, lesions, insects and other pests, disease symptoms, and other plant anomalies, for comparison with the transmitted images to help the diagnostic technician make an accurate diagnosis. The diagnostic station may additionally contain recommended treatments. After the diagnostic technician has made a diagnosis, this information is reported back to the workstation. The reporting may be done telephonically, by electronic mail, website, or by conventional mail.

After the diagnostic station has received the images, and a diagnosis has been made, the images, tagged field data, and diagnosis are stored and archived in a retrievable format. Preferably, the images are stored in an electronic format, so that they can be accessed by software programs with search capabilities. An exemplary software program for query-based searches is MICROSOFT ACCESS®.

The following Examples are offered by way of illustration and not by way of limitation.

EXAMPLE 1

Impact of Fungal Diseases on Seed Corn Production

Test strips were established at the Toledo, Reinbeck and Marengo, Iowa seed corn production location to determine the effect of foliar fungicide on seed quality and yield. The test strips were divided among three treatment groups: one application of a foliar fungicide, two applications of a foliar fungicide, and no treatment. The timing of application was determined by trained agronomists. Yield, moisture and seed quality were assessed for each treatment at the time of harvest.

Results indicate that seed corn yields were on average $7.1 \pm 3.2$ ($p=0.05$, $n=65$) saleable units (i.e., an 80,000 kernel bag of seed corn) per female acre greater in the treated areas as compared with the untreated areas. In one field, yields were decreased by 58% as a result of foliar disease. From this study, it was concluded that foliar diseases significantly decrease seed corn yields.

EXAMPLE 2

Establishing a Remote Site Pathology Laboratory

A remote site basic plant pathology (RSPP) laboratory was established at a Toledo, Iowa seed corn production facility. Toledo was chosen as the test site for the remote simple plant pathology laboratory based on several criteria. First, Toledo is only a two-hour drive from the central diagnostic facility in Johnston, Iowa. This proximity to Johnston is advantageous from the standpoint of ease in implementation. Second, Toledo is located in an area with a very high incidence of plant disease. Finally, Toledo is in the vicinity of two other seed corn production facilities in Reinbeck and Marengo, Iowa.

The RSPP laboratory at Toledo was equipped as follows:
AST Bravo P133 computer with 32 megabyte memory
Oculus-TCI flamegrabber interface board
MICROSOFT WORD® software program
an image management software program (L-VIEW PRO®—available on the internet at http://www.lview.com. Images can be annotated with specific field data (e.g., date image captured, inbred, field number, etc.).
an Olympus SZ40 series trinocular stereoscope with camera mount for viewing leaf disease symptoms (6.7× to 40× magnification).
an Olympus CH2 series trinocular microscope with internal light source and camera mount for viewing causal organisms (100×, 200×, and 400× magnification).
a Sony DXC-151A color video camera for acquiring images from the stereoscope and the microscope, or for use as a macroscope for acquiring images from whole plants.

light sources for the stereoscope.

a tripod used to stabilize the video camera for capturing images of plant samples where magnification is not necessary, for example, taking images of a root system or of a whole plant.

EXAMPLE 3

Remote Video Imaging

Fungal diseases in corn plants were diagnosed by remote video imaging from the Toledo RSPP laboratory using the following method. As the first step, samples of diseased plant tissue are cultured in between two pieces of filter paper in petri dishes at room temperature for 24 to 72 hours to promote sporulation of any pathogenic fungi present in the tissue lesions. After sufficient time for sporulation, the lesions in the tissue samples were observed under low magnification (6.7× to 40×) with a trinocular stereomicroscope. Microscopic slides were prepared by scraping the lesions to remove the causal pathogenic organisms. The pathogens were then observed under high magnification (100× to 400×) under the compound microscope. The stereomicroscope and compound microscope could both be mounted with color video cameras. Color video images were captured from both microscopes and stored on a AST Bravo P133 personal computer fitted with a framegrabber interface board. Manipulation and anotation of the images were done using L-VIEW Pro® software program. In some instances, macro views of the entire plant were acquired using the video camera alone.

Each image was annotated with relevant field data to assist the diagnostic technician in diagnosis. Data was collected and inputted into the computer using Microsoft Word® concerning field identification number, grower, inbred, weather conditions, field size, where lesion found, whether single plant or entire field is diseased, prior disease history in field. Images captured from the microscopes were inserted into the Microsoft Word® document. The data file accompanying each image also indicated who collected the sample and who should receive a copy of the diagnostic technician's report.

The stored color images and accompanying field data were transmitted to the Johnston pathology diagnostic facility in a single Microsoft Word® document using telephone lines. There the images and field data were called up and reviewed on a video monitor. In addition, hard copies of the images could be generated using a video printer. A pathologist at the Johnston facility made a diagnosis based on the transmitted images and field data, and reported the diagnosis back to the Toledo RSPP laboratory. The images and relevant data were then archived within Microsoft Word®, where they can be retrieved for use in diagnosing other plant samples.

EXAMPLE 4

Results Achieved by Remote Video Imaging

Diagnosis of corri plant pathogens was performed using the remote imaging diagnosis system described in Examples 2 and 3. When the RSPP laboratory at Toledo was first established, samples were analyzed both by remote video imaging from Toledo and by sending a "hard" sample to Johnston for conventional diagnosis. In this manner, the accuracy of remote video imaging could be assessed. In a one-year period, a total of 130 samples were processed through the Toledo RSPP laboratory, with 100% accuracy in diagnosis. Samples were taken from the Toledo, as well as, Marengo and Reinbeck seed production locations.

The first disease diagnosed using remote video imaging was Northern Corn Leaf Spot (*Helminthosporium carbonum*, Syn. *Bipolaris zeicola*). An image of the causal organism was transmitted to the Johnston facility through communication (telephone) lines. Verification of the causal organism was confirmed within one-half hour by Johnston-based pathologists. Using conventional methods (i.e., sending a sample to Johnston by car or U.S. mail), the diagnosis would have taken up to 3 or 4 days.

Diagnosis of other cultured samples from the Toledo RSPP laboratory indicated Gray Leaf Spot (*Cercospora zeae-maydis*), Northern Corn Leaf Spot (*H. carbonun*), and common rust (*Puccinia sorghi*) as the major corn diseases in this area (Table I). It was not previously realized that Northern Corn Leaf Spot was so prevalent in the area. Moreover, the data collected by remote video imaging led to early detection of Northern Corn Leaf Spot and indicated that the disease was quite severe in some seed corn fields. As a result, a foliar fungicide was applied within 2 days of diagnosis. Furthermore, the diagnosis of Northern Corn Leaf Spot was communicated to other seed corn locations growing the same female parent to alert them to the potential problem. This level of reporting has not been feasible in the past because the central pathology laboratory in Johnston does not know which locations are growing particular inbreds. Non-pathogenic lesions, such as genetic heat stripe, were also identified using remote video imaging from the RSPP laboratory at Toledo.

EXAMPLE 5

Remote Imagery Use for Wheat

Wheat can be inflicted by many diseases that can dramatically reduce yield or seed quality but one of the most devastating diseases for a seed crop is caused by *Fusarium graminearum* (*Gibberella zeae*). Early detection of infection by this pathogen allows for the development of an appropriate fungicide spray program. Proper control of this disease can dramatically lower the losses to the seed crop.

Glumes and immature seed are cultured at the remote site and the resulting fungal structures are imaged. The images are transmitted to the Diagnostic station where identification is made. Upon positive identification a spray program is put in place reducing losses and retaining the quality of the seed.

EXAMPLE 6

Remote Imagery Use for Soybean

Several diseases of soybeans are potentially economically damaging to a seed crop. Proper spraying of fungicides at the critical time can greatly lower the damage to seed quality. *Phomopsis sojae* (pod and stem blight) can reduce seed quality through pod infections. Identification of the presence of Phomopsis at an early stage can allow for a proper fungicide spray program to be initiated.

Detection of Phomopsis on soybean stems is an early indication of potential pod infection. Stems are cultured by the remote sites and images taken of the pycnidia and conidia. Images are transmitted to the pathologist and positively identified using the combination of images.

Upon positive identification a fungicide spray program is implemented. Losses due to reduced yield and/or poor quality seed are dramatically reduced.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

TABLE I

Diagnosis of Corn Plant Disease
by Remote Video Imaging from the RSPP Laboratory at Toledo, Iowa

| Disease | Number of Cultures | Percent of Cultured Samples |
| --- | --- | --- |
| Gray leaf spot | 53 | 41% |
| Northern corn leaf spot | 35 | 27% |
| Common rust | 17 | 13% |
| Other[1] | 25 | 19% |

[1]Samples included eyespot, anthracnose, genetic heat stripe, no disease, etc.

That which is claimed:

1. A remote imaging system for diagnosing plant anomalies comprising:
   (a) a remote workstation, said workstation comprising a means for videomicroscopy;
   (b) a diagnostic station, said diagnostic station having means for receiving images transmitted from said remote workstation, viewing means for displaying said images, a database of plant anomalies for comparison with said images, and archiving means for storing said images in a retrievable format; and
   (c) a transmission means for sending said images from said remote workstation to said diagnostic station.

2. A remote imaging system according to claim 1, wherein said workstation comprises a stereomicroscope for viewing a sample taken from a plant, a compound microscope for viewing causal organisms present in said sample, and a video camera, mounted to said stereomicroscope and said compound microscope, for acquiring images therefrom, and a digital microprocessor with a framegrabber board for capturing images.

3. A remote imaging system according to claim 2 wherein said remote workstation further comprises means for manipulating said stereomicroscope and said compound microscope from said diagnostic station.

4. A remote imaging system according to claim 1 further comprising a macroscope for capturing non-magnified images of a diseased plant.

5. A remote imaging system according to claim 1 wherein field data are transmitted along with said images.

6. A remote imaging system according to claim 1 wherein said images are displayed and viewed in real time at said diagnostic station.

7. A remote imaging system system according to claim 1, wherein said plant anomaly is selected from the group consisting of genetic abnormality, insect injury, chemical injury, environmental injury, and plant disease.

8. A remote imaging system according to claim 7 wherein said plant disease is a pathogenic disease.

9. A remote imaging system according to claim 8 wherein said plant pathogenic disease is a fungal disease.

10. A remote imaging system according to claim 8 wherein said plant pathogenic disease is a foliar disease.

11. A remote imaging system according to claim 1 wherein said plant is a crop plant.

12. A remote imaging system according to claim 11, wherein said crop plant is corn.

13. A method of diagnosing plant anomalies comprising:
   (a) preparing a sample from a plant at a remote location, said sample preparation comprising removing tissue from said plant;
   (b) viewing said sample with a stereomicroscope;
   (c) capturing images from said stereomicroscope and a compound microscope with a videocamera and microprocessor with a framegrabber board located at a remote workstation;
   (d) transmitting said captured images to a diagnostic station;
   (e) displaying said images at said diagnostic station; and
   (f) diagnosing said plant anomaly from said displayed images.

14. A method according to claim 13 further comprising the step of comparing said image received at said diagnostic station with images stored in a database of plant anomalies.

15. A method according to claim 13 further comprising:
   (a) capturing non-magnified images of said plant with a macroscope and microprocessor with a framegrabber board at a remote workstation; and
   (b) transmitting said images collected with said macroscope to said diagnostic station.

16. A method according to claim 13 wherein field data are transmitted along with said images.

17. A method according to claim 13 wherein said images are displayed and viewed in real time at said diagnostic station.

18. A method according to claim 13 wherein said plant anomaly is a plant disease.

19. A method according to claim 18 wherein said plant disease is a pathogenic disease.

20. A method according to claim 19 wherein said plant pathogenic disease is a fungal disease.

21. A method according to claim 18 wherein said plant disease is a foliar disease.

22. A method according to claim 13 wherein said plant is a crop plant.

23. A method according to claim 22 wherein said crop plant is corn.

24. A method of diagnosing fungal diseases in plants comprising:
   (a) preparing a sample from a diseased plant at a remote location, said sample preparation comprising the steps of:
      (i) removing tissue bearing lesions from said diseased plant;
      (ii) culturing said tissue under conditions sufficient to promote the sporulation of any fungi present in said lesion;
   (b) viewing said cultured tissue with a stereomicroscope;
   (c) preparing a microscope slide of fungi from said cultured tissue;
   (d) viewing said fungi from said cultured tissue with a compound microscope;
   (e) capturing images from said stereomicroscope and said compound microscope with a videocamera and a microprocessor with a framegrabber board located at a remote workstation;
   (f) transmitting said captured images to a diagnostic station;

(g) displaying said images at said diagnostic station; and (h) diagnosing said fungal disease from said displayed images.

25. A method according to claim 24 further comprising the step of comparing said image received at said diagnostic station with images stored in a database of plant pathogens and lesions.

26. A method according to claim 24 further comprising:

(a) capturing non-magnified images of said diseased corn plant with a macroscope and microprocessor with a framegrabber board at said remote workstation; and (b) transmitting said images collected with said macroscope to said diagnostic station.

27. A method according to claim 24 wherein field data are transmitted along with said images.

28. A method according to claim 24 wherein said plant is a crop plant.

29. A method according to claim 28 wherein said crop plant is corn.

30. A remote imaging system for diagnosing plant anomalies comprising:

(a) a remote workstation, said workstation comprising a stereomicroscope for viewing a sample taken from a plant, a compound microscope for viewing causal organisms present in said sample, and a video camera, mounted to said stereomicroscope and said compound microscope, for acquiring images therefrom, and a digital microprocessor with a framegrabber board for capturing images; and (b) a diagnostic station, said diagnostic station having means for receiving images transmitted from said remote workstation, viewing means for displaying said images, a database of plant anomalies for comparison with said images, and archiving means for storing said images in a retrievable format; and (c) a transmission means for sending said images from said remote workstation to said diagnostic station.

31. A remote imaging system according to claim 30 further comprising a macroscope for capturing non-magnified images of a diseased plant.

32. A remote imaging system according to claim 30 wherein field data are transmitted along with said images.

33. A remote imaging system according to claim 30 wherein said remote workstation further comprises means for manipulating said stereomicroscope and said compound microscope from said diagnostic station.

34. A remote imaging system according to claim 30 wherein said images are displayed and viewed in real time at said diagnostic station.

35. A remote imaging system according to claim 30, wherein said plant anomaly is selected from the group consisting of genetic abnormality, insect injury, chemical injury, environmental injury, and plant disease.

36. A remote imaging system according to claim 35 wherein said plant disease is a pathogenic disease.

37. A remote imaging system according to claim 36 wherein said plant pathogenic disease is a fungal disease.

38. A remote imaging system according to claim 36 wherein said plant pathogenic disease is a foliar disease.

39. A remote imaging system according to claim 30 wherein said plant is a crop plant.

40. A remote imaging system according to claim 39, wherein said crop plant is corn.

* * * * *